US006051757A

United States Patent [19]
Barton et al.

[11] Patent Number: 6,051,757
[45] Date of Patent: Apr. 18, 2000

[54] REGENERATION OF PLANTS CONTAINING GENETICALLY ENGINEERED T-DNA

[75] Inventors: Kenneth Allen Barton, Madison, Wis.; Andrew Norton Binns, Philadelphia, Pa.; Mary-Dell Matchett Chilton, University City, Mo.; Antonius J. M. Matzke, Salzburg, Austria

[73] Assignee: Washington University, St. Louis, Mo.

[21] Appl. No.: 08/464,542

[22] Filed: Jun. 5, 1995

Related U.S. Application Data

[63] Continuation of application No. 07/155,092, Feb. 11, 1988, which is a continuation of application No. 06/817,411, Jan. 9, 1986, abandoned, which is a continuation of application No. 06/458,033, Jan. 14, 1983, abandoned.

[51] Int. Cl.$^7$ .......................... C12N 15/82; C12N 15/84; A01H 1/04
[52] U.S. Cl. .......................... 800/294; 800/260; 435/469
[58] Field of Search ................................. 800/205, 250, 800/294, 260; 435/172.3, 252.2, 240.4, 419, 469; 47/58, DIG. 1

[56] References Cited

PUBLICATIONS

Potrykus, I. Bio/Technology 8(6):535–542, 1990.
Goodman et al. Scence 236: 48–54, Apr. 1987.
Hernalsteens et al. 1984. EMBO J 3(13): 3039–3041.
Lippincott et al. 1978. Science 199: 1075–1078.
De Cleene, M. 1985. Phytopath Z. 113 : 81–89.
DeCleene et al. 1976. Bot. Rev. 42(4): 389–466.
Bohn, G.W. and C.M. Tucker, Science 89, pp. 603–604 (1939).
Dudits, et al., "Plant regeneration from intergeneric cell hybrids", Plant Sci. Lett., 15, pp. 101–112 (1979).
Dudits, et al., "Backfusion with somatic protoplasts as a method in genetic manipulation of plants", Acta. Biol. Acad. Sci. Hung, 32, pp. 215–218 (1981).
Hoffman, et al., "Arabidobrassica: chromosomal recombination and morphogenesis in asymmetric intergeneric hybrid cells", Planta (Berlin), 153, pp. 586–593 (1981).
Leemans, J. et al., "Site–Specific Mutagenesis of Agrobacterium Ti Plasmids and Transfer of Genes to Plant Cells," J. Mol. Appl. Genet. vol. 1, No. 2: pp. 149–164 (1981).
Leemans, J. et al., "Ti Plasmids and Genetic Engineering," Molecular Biology of Plant Tumors, Chapter 21: pp. 537–545 (Jan. 28, 1982).
Melchers, et al., "Somatic hybrid plants of potato and tomato regenerated from fused protoplasts", Carlsberg Res. Commun., 43, pp. 203–218 (1978).
Newell, C.A. and R. Hymowitz, Crop Sci. 22, pp. 1062–1065 (1982).
Poulsen, et al., "Peptide mapping of the ribulose bisphosphate carboxylase small subunit from the somatic hybrid of tomato and potato", Carlsberg Res. Commun., 45, pp. 249–267 (1980).
Schiller, et al., "Restriction endonuclease analysis of plastid DNA from tomato, potato and some of their somatic hybrids", Mol. Gen. Genet., 186, pp. 453–459 (1982).

Van Montagu, M. et al., "The Ti Plasmids of Agrobacterium," Current Topics in Microbiology and Immunology vol. 96: pp. 237–254 (Dec. 21, 1981).
Marton et al., Nature vol. 277, pp. 129–131 (1979).
Wullems et al., Cell, vol. 24, pp. 719–727 (Jun. 1981).
Binns, "Oxford Surveys of Plant Molecular & Cell Biology," vol. 1, pp. 133–160 (1984) (see page 149).
Bennetzen and Hall, J. Biol. Chem., 257: 3026–3031 (1982).
Bevan and Chilton, J. Mol. Appl. Genet., (1982).
Binns et al., Differentiation, 19: 97–102 (1981).
Chilton et al., Nature (London), 295: 432–34 (1982).
Chilton et al., Nature (London), 275: 147–149 (1978).
Chilton, et al., Cell, 11: 263–71 (1977).
Chilton, et al., Proc. Natl. Acad. Sci. [USA], 77: 2693–97 (1980).
Ditta et al., Proc. Natl. Acad. Sci. [USA], 77: 7347–51 (1980).
Guyon et al., Proc. Natl. Acad. Sci. [USA], 77: 2693–97 (1980).
Hernalsteens et al., Nature (London), 287: 654–56 (1980).
Holsters et al., Mol. Gen. Genet., 163: 181–87 (1978).
Jorgensen et al., Mol. Gen. Genet., 177: 65–72 (1979).
Matzke and Chilton, J. Mol. App. Genet., 1: 39–49 (1981).
Montoya et al., J. Bacteriol., 129: 101–07 (1977).
Murashige and Skoog, Physiol. Plant., 15: 473–497 (1962).
Sciaky et al., Plasmid, 1: 238–53 (1978).
Thomashow et al., Proc. Natl. Acad. Sci. [USA], 77: 6448–52 (1980).
Willmitzer et al., Nature (London), 287: 359–61 (1980).
Wood et al., Differentiation, 11: 175–80 (1978).
Yadav et al., Nature (London), 287: 458–61 (1980).
Yadav et al., Proc. Natl. Acad. Sci. [USA], 79: 6322–6326 (1982).

(List continued on next page.)

*Primary Examiner*—David T. Fox
*Attorney, Agent, or Firm*—White & Case LLP

[57] ABSTRACT

Inactivation of the cytokinin autonomy gene of T-DNA in broad host range Ti plasmid produces mutant T-DNA vectors suitable for insertion of foreign genes; insertion of the mutant T-DNA by an in vitro tissue culture technique or any other technique into plant cells produces genetically engineered plant cells that can be regenerated into complete plants with roots. The inactivation of the cytokinin autonomy gene disarms the Ti plasmid and produces a useful gene vector for higher plants. The inactivation of the cytokinin gene may be accomplished by techniques such as point mutation, inversion, deletion, transposition, substitution or insertion. In the case of tobacco, for example, transformation of tobacco stem segments with engineered bacterial strains resulting from the insertion of DNA encoding yeast alcohol dehydrogenase and a bacterial neomycin phosphotransferase into the T-DNA of *Agrobacterium tumefaciens* plasmid pTiT37 at the "rooty locus" produced transformed plant cells that were capable of regeneration into intact, normal tobacco plants. The yeast gene and entire T-DNA were present in the regenerated plants in multiple copies, and nopaline was found in all tissues. The plants were fertile and seedlings resulting from self-pollination also contained intact and multiple copies of the engineered T-DNA.

20 Claims, 7 Drawing Sheets

OTHER PUBLICATIONS

Yang et al., *Mol. Gen. Genet.,* 177: 704–14 (1980).
Zambryski et al., *Science,* 209: 1385–91 (1980).
BenneLzen and Hall, *J. Biol. Chem.,* 257: 3018–3025 (1982).
Binns and Meins, *Planta,* 145: 365–369 (1979).
Bomhoff et al., *Mol. Gen. Genet.,* 145: 177–181 (1976).
Braun and Wood, *Proc. Natl. Acad. Sci.* [USA], 73: 496–500 (1976).
Braun, *Am. J. Bot.,* 334: 234–240 (1947).
Braun, *Cancer Res.,* 16: 53–56 (1956).
Currier and Nester *J. Bacteriol.,* 126: 157–65 (1976).
Depicker et al., *Nature,* 275: 150–52 (1978).
Murai & Kemp, *Proc. Natl. Acad. Sci.* [USA], 79: 86–90 (1982).
Otten and Shilperoort, *Biochim. Biophys. Acta,* 527: 497–500 (1978).
Petit et al., *Physiol. Veg.,* 8: 205–13 (1970).
Ruvkin and Ausubel, *Nature* (London), 289: 85–88, (1980).
Schroeder et al., *FEBS Lett.,* 129: 166–68 (1981).
Turgeon et al., *Proc. Natl. Acad. Sci.* [USA], 73: 3562–64 (1976).
Williamson et al., *Nature* (London), 283: 214–216 (1980).
Wullems et al., *Proc. Natl. Acad. Sci.* [USA], 78: 4344–48 (1981).

REGENERATED PLANTS CONTAIN YEAST ADH-1 GENE

Bam HI DIGESTS

T-DNA IN F1 PROGENY PLANTS

Eco RI DIGESTS

REGENERATED PLANTS CONTAIN FULL LENGTH T-DNA

EcoRI DIGESTS

REGENERATED PLANTS CONTAIN FULL LENGTH T-DNA

BamHI DIGESTS

REGENERATION OF PLANTS CONTAINING GENETICALLY ENGINEERED T-DNA

This application is a continuation of Application Ser. No. 07/155,092, filed on Feb. 11, 1988, which is a continuation of application Ser. No. 06/817,411, filed Jan. 9, 1986 (abandoned), which is a continuation of application Ser. No. 06/458,033, filed on Jan. 14, 1983 (abandoned).

BACKGROUND OF THE INVENTION

This invention relates to the field of plant genetic engineering and, more particularly, to the regeneration of complete plants containing full length copies of genetically engineered T-DNA and the transmission of T-DNA to R1 progeny.

Ti plasmids of the plant pathogen *Agrobacterium tumefaciens* have the unique natural ability to transform cells of susceptible host plants by the insertion of an 8 to 23 kilobase (kb) sector of plasmid DNA into host chromosomal DNA (Chilton et al., Cell 11:263–71 (1977); Chilton et al., Proc. Natl. Acad. Sci. USA, 77:2693–97 (1980); Willmitzer et al., Nature (Lond.) 287:359–61 (1980); Yadav et al., Nature (Lond.) 287:458–61 (1980); and Zambryski et al., Science 209:1385–91 (1980)). This transferred DNA (T-DNA) causes the transformed cells to synthesize new metabolites called opines (Petit et al., Physiol. Veg., 8:205–13 (1970); Bomhoff et al., Mol. Gen. Genet. 145:177–181 (1976); and Montoya et al., J. Bacteriol., 129:101–07 (1977)). The synthase enzyme for one opine, octopine, has recently been shown to be encoded by a T-DNA gene (Murai and Kemp, Proc. Natl. Acad. Sci. USA, 79:86–91 (1982); and Schroder et al., FEBS Lett., 129:166–68 (1981)). Additional genes in T-DNA affect the phytohormone balance of transformed cells as evidenced by altered morphology of tumor cells transformed by various mutant T-DNAs (Ooms et al., Gene, 14:33–50 (1981); and Garfinkel et al., Cell, 27:143–153 (1981)). Transformed plant cells containing wild type T-DNA grow in vitro without an exogenous supply of either auxin or cytokinin (Braun, Am. J. Bot., 34:234–240 (1947)), whereas normal plant cells usually require both substances for growth in culture. Mutations in one T-DNA locus cause tumors from which abundant roots proliferate ("rooty" mutants), while mutations in a second T-DNA locus cause tumors from which shoots proliferate ("shooty" mutants) (Ooms et al., supra, Garfinkel et al., supra). Transformation of tobacco cells by shooty mutant T-DNA results in tumors which exhibit a complex auxin requirement. Such tissues will grow on hormone free medium under conditions which allow shoot proliferation, but otherwise require auxin for continuous growth (Binns et al., Cell (1982)). The rooty and shooty functions map in a T-DNA region common to octopine, nopaline, "unusual nopaline" and agropine Ti plasmids of wide host range (Chilton et al., Nature, 275:147–149 (1978); Depicker et al., Nature, 275:150–52 (1978); Engler et al., J. Mol. Biol., 152:183–208 (1981); and Guyon et al., Proc. Natl. Acad. Sci., 77:2693–97 (1980), evidence that all such Ti plasmids promote oncogenic growth of plant cells through a common mechanism.

T-DNA acts as a natural gene vector for *A. tumefaciens,* producing transformed plant cells that display an abnormal hormonal balance and synthesize new metabolites. Recent work has shown that the Ti plasmid can be exploited as an artificial gene vector to introduce novel genes into plant tumor cells (Hernalsteens et al., Nature, 287:654–656 (1980); and Leemans et al., EMBO Journal, 1:147–52 (1982)). Heretofore, a major obstacle to the exploitation of Ti plasmids as gene vectors for higher plants has been the difficulty of regeneration of whole plants from transformed plant cell lines. Cloned teratomatous lines of tobacco cells containing wild type nopaline plasmid pTiT37 T-DNA spontaneously or upon cytokinin induction regenerated shoots that displayed varying degrees of normalcy upon grafting onto healthy host plants (Braun and Wood, Proc. Natl. Acad. Sci., 73:496–500 (1976); Turgeon et al., Proc. Natl. Acad. Sci., 73:3562–64 (1976); and Binns et al., Differentiation 19:97–102 (1981)). Such shoots synthesized nopaline (Wood et al., Differentiation 11:175–80 (1978)), failed to form roots, and were resistant to superinfection by *A. tumefaciens* (Braun and Wood, supra; Turgeon et. al., supra; and Binns et al., supra). When fertile, these grafted shoots produced seed that gave rise to apparently normal plants that lacked nopaline, produced roots and were sensitive to *A. tumefaciens* (Braun and Wood, supra; Turgeon et al., supra; Binns et al., supra). Indeed, the cells of one such plant were shown to be completely free from T-DNA (Yang et al., Mol. Gen. Genet., 177:704–14 (1980); Lemmers et al., J. Mol. Biol., 144:353076 (1980)). Similar results have been obtained in studies of tobacco cells transformed in vitro by either octopine or nopaline type T-DNA (Wullems et al., Proc. Natl. Acad. Sci. 78:4344–48(1981a); Cell, 24:719–28 (1981b)). In such experiments, opine-positive plant cells with roots were not obtained, and shoots obtained by grafting were usually both opine-positive and resistant to superinfection by *A. tumefaciens.* A single example has been reported of opine-positive complete plants regenerated from a crown gall tumor initially incited by a shooty mutant of octopine T-DNA (Leemans et al., supra). These plants segregated the octopine trait in Mendelian fashion to healthy progeny, evidence that T-DNA was situated in chromosomes of the parental tissue. However, the T-DNA in these plants was found not to be full length. A large deletion of the central part of T-DNA apparently gave rise to plant cells with little T-DNA except for the octopine synthase gene.

There has thus been a failure of past efforts to regenerate whole plants containing intact T-DNA. Such efforts have produced instead plants whose T-DNA has been almost completely deleted.

SUMMARY OF THE INVENTION

Among the objects of the present invention may be noted the provision of mutant T-DNA vectors useful in producing transformed plant cells that can be regenerated into complete plants with roots; the provision of such mutant T-DNA vectors that are characterized by having the function of the cytokinin autonomy gene therein inactivated; the provision of such vectors that are avirulent on Kalanchoe leaves; the provision of transformed plant cells, seeds and plants which contain said mutant T-DNA, the plant cells, if unorganized, requiring exogenous cytokinin for growth; and the provision of methods for producing such mutant T-DNA vectors and for regenerating genetically engineered complete plants with roots. Other objects and features will be in part apparent and in part pointed out hereinafter.

Briefly, the present invention in one aspect is directed to a method for regenerating genetically engineered complete plants with roots by inactivating the cytokinin autonomy gene of T-DNA in broad host range Ti plasmids to produce mutant T-DNA vectors and inserting the mutant T-DNA by an in vitro tissue culture technique or any other technique into plant cells to produce genetically engineered plant cells that can be regenerated into complete plants with roots. In other aspects, the invention is directed to a method for producing such mutant T-DNA vectors and the use of such mutant T-DNA vectors for in turn producing novel plant cells, plant seeds and plants in all of which the T-DNA vectors are characterized by having the function of the cytokinin autonomy gene therein inactivated and by being avirulent on Kalanchoe leaves.

DESCRIPTION OF PREFERRED EMBODIMENTS

Figure 1:
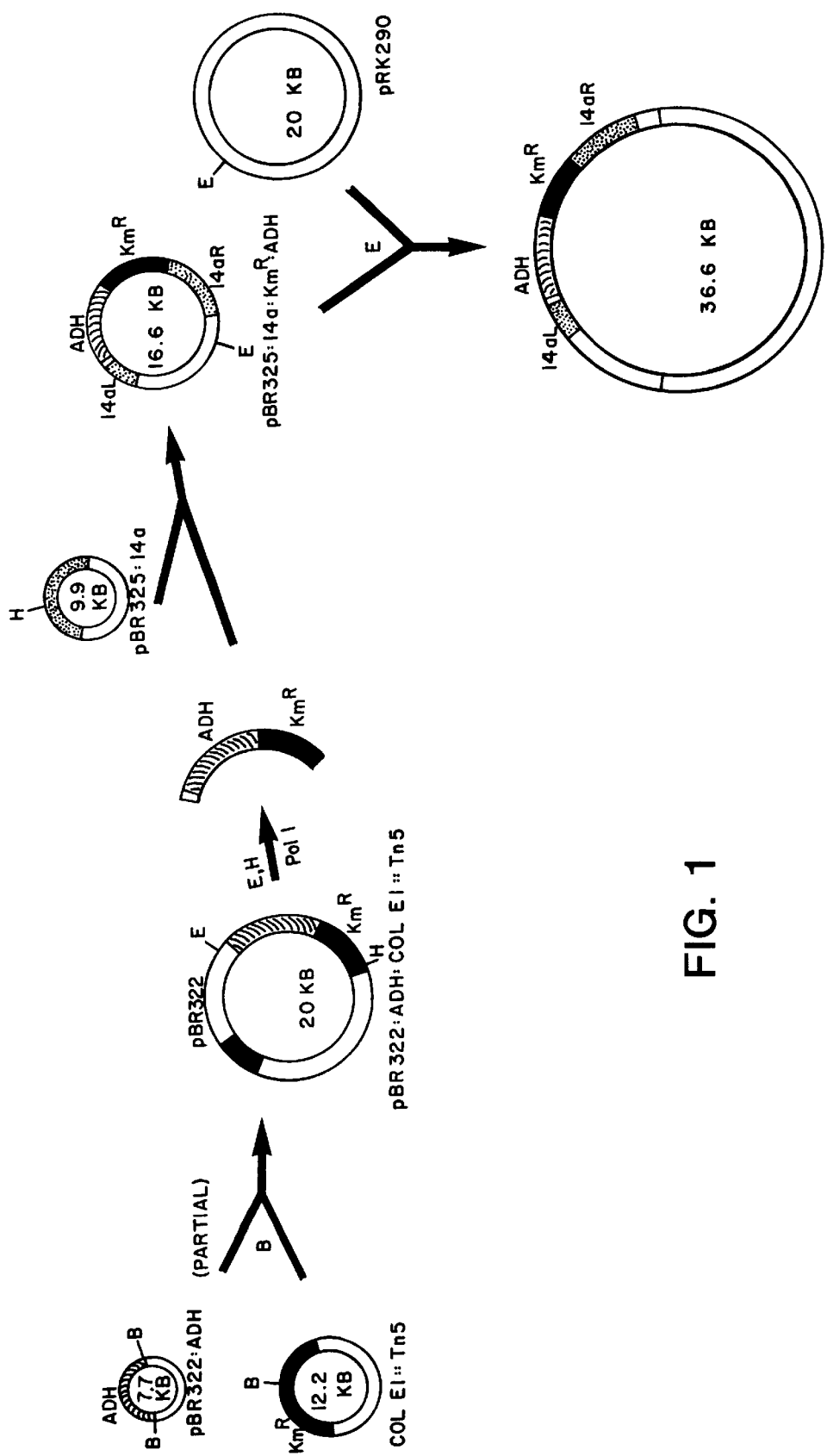
FIG. 1 is a schematic showing of the construction of an engineered wide host range plasmid for use in the invention.

In accordance with the present invention, we have now discovered that practical means for regenerating complete plants with roots are achieved through the key step of inactivating the cytokinin autonomy gene of T-DNA in broad host range Ti plasmids thereby disarming the plasmids to produce effective and useful genetic engineering vectors. The term "cytokinin autonomy gene" as used herein to describe a T-DNA gene is intended to mean that if the gene is functioning in the plant cell, the cell will be cytokinin autonomous. This discovery is based on our recognition of the fact that the cytokinin autonomy gene is responsible for making tumor cells grow autonomously, such cells being unable to produce developmentally normal plants, and in turn that the elimination of this gene or the function of this gene (i.e. "disarming" of T-DNA) permits the regeneration of complete plants with roots containing one or more full length copies of genetically engineered T-DNA as constructed in the inciting bacterium.

The Agrobacterium Ti plasmid, as is known, acts in nature as a gene vector and has the natural ability to bring about insertion of a specific part of the plasmid, denoted as T-DNA, into the chromosomal DNA of plant cells. The result of such gene insertion is that the plant cells grow as non-self limiting transplantable tumors. Such tumor cells, unlike normal plant cells, are not able to regenerate into whole plants with roots.

Through the present invention, we have found that it is practical to "disarm" T-DNA and specifically eliminate the gene that prevents plant regeneration. Depending upon the particular Ti plasmid, there are some 10 to 15 genes situated in T-DNA. Five of these genes are common to all wide or broad host range Ti plasmids we have studied. Four of these genes affect tumor morphology or size in ways that are believed to cause plant hormone disturbances. It is also believed that these are the tumor-inducing genes and elimination of all of these genes by genetic deletion does indeed eliminate tumor formation.

We have discovered, in accordance with the invention, that the cytokinin autonomy gene is the key gene of the five common genes above-mentioned, whose inactivation is essential to the disarming of T-DNA. Tumor cells have elevated levels of auxin and cytokinin that are believed to prevent regeneration of plant cells to whole plants. The inactivation of a single gene in T-DNA, namely, the cytokinin autonomy gene, produces two important consequences in the application of our invention, for example, to tobacco cells.

1. Transformed (genetically engineered) tobacco cells containing the mutant T-DNA having the function of the cytokinin autonomy gene therein eliminated are like normal tobacco cells in cytokinin requirement: they absolutely require exogenous cytokinin for growth in tissue culture as a callus tissue. Tumor cells synthesize cytokinin spontaneously in culture. Since cytokinin is the cell-division factor in plants, this cytokinin autotrophy of tumor cells is apparently responsible for their uncontrolled or tumorous cell division.

2. Transformed tobacco cells containing the mutant T-DNA are like normal tobacco cells in that they can be regenerated into complete plants with roots.

The mutant or disarmed form of T-DNA produced through the practice of our invention yields the following results, for example, in the case of tobacco cells.

1. Regenerated tobacco plants from several cell lines containing such mutant T-DNA synthesize nopaline, a metabolite whose synthesis is conferred by an innocuous T-DNA gene. The plants examined contained full-length copies of T-DNA.

2. The T-DNA in the regenerated plants we have examined is present in multiple copies (more than 10 copies per plant cell). This provides evidence that the remainder of the T-DNA is indeed innocuous to tobacco plants.

3. The regenerated plants have fertile gametes and produce viable seeds upon being self-pollinated.

4. The plants grown up from these seeds contain multiple copies of full-length T-DNA in the plants examined.

5. The genetically engineered tobacco plants produced through the present invention contain multiple copies of the foreign gene insert by which the mutant or disarmed T-DNA is produced.

In general, the mutant T-DNA or inactivation of the cytokinin autonomy gene may be produced by the insertion of foreign genes into the cytokinin gene of T-DNA. In the case of the tobacco plants described here for purposes of illustration, the mutant T-DNA is produced by inserting into the cytokinin autonomy gene of pTiT37 T-DNA two foreign genes, namely, the yeast alcohol dehydrogenase I gene and a bacterial gene encoding neomycin phosphotransferase (kanamycin resistance). It will be understood that other foreign genes may also be utilized for the purpose of inactivating the cytokinin autonomy gene and producing a disarmed T-DNA vector.

In lieu of the insertion of foreign genes, other techniques known to the art such as deletion, inversion, point mutation, transposition and substitution may be used to eliminate or inactivate the function of the cytokinin autonomy gene and achieve the objectives of the invention. The step of inactivating the cytokinin gene is the key to disarming broad host range Ti plasmids for use as genetic engineering vectors. All plants regenerated thus far from tumor cells have eliminated the function of this gene and no plants have been regenerated in which this gene survives intact. It is thus believed that inactivation of this gene is sufficient to disarm the T-DNA vector.

On the basis of our work, it is believed that the invention is applicable to all four known groups or types of broad host range Ti plasmids, namely, the nopaline, "unusual nopaline", octopine and agropine types or to any plasmid which does not have an affinity for a specific type of host plant. The T-DNA portion of such plasmids shares common DNA and the cytokinin autonomy gene forms a part of that common DNA. In the case of the nopaline and octopine types, the cytokinin gene produces a transcript (messenger RNA) 1,200 bases long that has been mapped. A similar gene and transcript are believed to exist in the "unusual nopaline" and agropine type Ti plasmids since these possess common DNA homologous to this gene. These broad host range Ti plasmids are believed to represent the most important candidates for the production of mutant T-DNA gene vectors for regeneration of a wide range of plants such as tobacco, several other Nicotiana species, carrot, cauliflower, convolvulus, etc. Thus, the present invention makes possible widespread regeneration of plants from the rooty mutant tumors produced thereby.

As mentioned inactivation of the cytokinin autonomy gene can be achieved through insertion of foreign genes, i.e. insertion of foreign DNA at a certain site in the cytokinin gene, or through other forms of manipulation such as deletion. In the case of tobacco and the nopaline type Ti plasmid pTiT37, the size of the messenger RNA from the "rooty locus" or cytokinin gene is 1,200 bases as determined by "northern" blot analysis of the polyadenylated (mature) messenger RNA. The 5' (beginning) end of the messenger RNA lies 700 bases to the left of the Hpa I site in Bam HI fragment 14a of pTiT37. The cytokinin gene is presumed to extend several hundred bases leftward from the 5' end of the message. The 3' end (terminus) of the RNA therefore lies approximately 500 bases to the right of the Hpa I site above-mentioned. Accordingly, the insertion of foreign genetic information into the Hpa I site of pTiT37 Bam HI fragment 14a at this particular location causes tumors to lose cytokinin autotrophy and produces a "rooty" phentotype or mutant T-DNA for use in the present invention. The particular location for insertion of foreign genes for inactivation of the cytokinin gene in the other two types of broad host range Ti plasmids can be determined by DNA sequencing of the homologous region of T-DNA in such plasmids.

The mutant T-DNA produced by inactivation or elimination of the function of the cytokinin autonomy gene is characterized by being avirulent (no visible tumor) on *Kalanchoe daigremontiana* plant leaves and causing rooty tumors on *Kalanchoe daigremontiana* stems. Also, the mutants incite transformed roots on carrot discs.

For the purpose of regenerating complete genetically engineered plants with roots, the mutant T-DNA is inserted into plant cells, for example, by any technique such as in vivo inoculation or by any of the known in vitro tissue culture techniques to produce transformed plant cells that can be regenerated into complete plants. Thus, for example, the insertion into plant cells may be by in vitro inoculation by pathogenic *A. tumefaciens*. Other such tissue culture techniques may also be employed.

The illustrative experimental data and results presented hereinafter relate to the regeneration of plants from tobacco cells transformed by rooty mutants of pTiT37 in accordance with the invention. As stated, directing the insertion of foreign DNA into the Hpa I site in pTiT37 Bam HI fragment 14a, which is in the rooty locus or cytokinin autonomy gene on nopaline-type T-DNA, effectively overcomes the problem of regeneration of plants from transformed cells. The results presented hereinafter demonstrate that engineered Ti plasmids with such a mutation induce attenuated crown gall tumors that are not cytokinin autotrophic as are wild-type T37 induced tumors. Moreover, the cloned transformed tobacco cells containing such mutant T-DNA are prone to both root initiation and regeneration of intact plants.

The plants regenerated from both HADH2 and H14a/a transformed cell lines appear quite normal, with only minor morphological differences from wild-type plants, such as slightly elongated stigmas. It is possible this results from the presence of T-DNA in the cells, but such differences may also be due to passage of the cells through tissue culture. The presence of nopaline in all tissues of the regenerated plants indicates that at least one T-DNA gene, that encoding nopaline synthase, remains functional. The plant cells appear to be capable of either regulating T-DNA genes or modulating auxin levels efficiently, allowing the growth and development of normal plants.

The plants regenerated through the practice of the present invention transmit full length T-DNA to their normal R1 progeny, have fertile gametes and produced viable seeds upon being self-pollinated.

The following illustrates the practice of the invention.

1. Site specific Insertion of Yeast ADH I into the T-DNA of pTiT37

The large size of plasmid pTiT37 precludes the direct introduction of foreign DNA sequences into a precise position within the T-DNA. The gene encoding yeast alcohol dehydrogenase I (ADH I) (Williamson et al., Nature, 283: 214–216, 1980; Bennetzen and Hall, J. Biol. Chem., 257:3018–3025, 1982 and Bennetzen and Hall, J. Biol. Chem., 257: 3026–3031, 1982) was accordingly introduced into a specific restriction site within the T-DNA by the indirect technique of Matzke and Chilton, J. Mol. App. Genet., 1:39–49 (1981), as shown in FIGS. 1 and 2.

Figure 2:
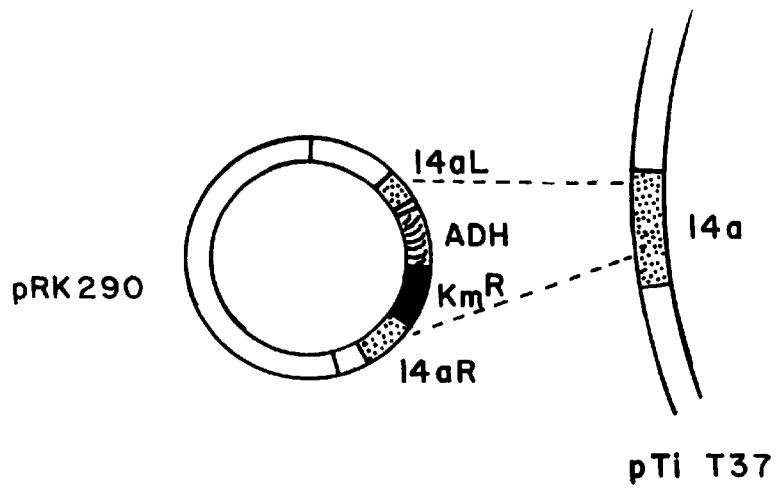
FIG. 2 is a schematic showing of the exchange of the engineered T-DNA subfragment onto pTiT37.
Figure 2:
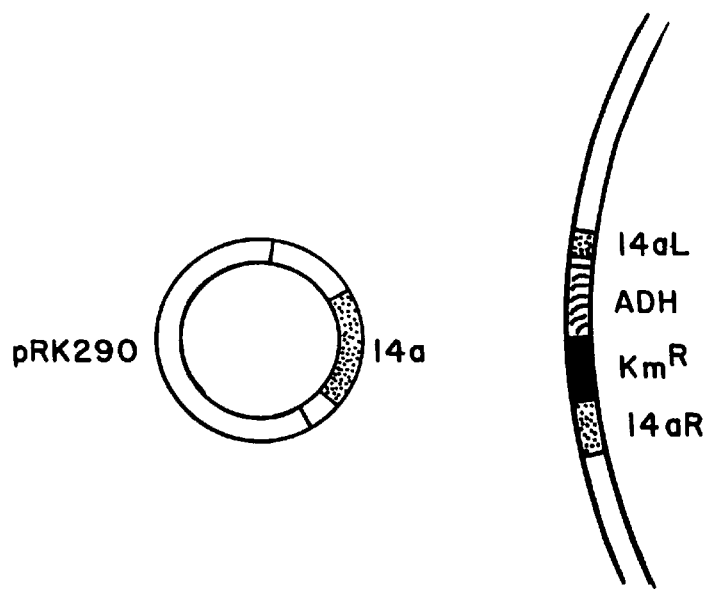

Referring to FIG. 1 and the information therein, it is shown that the engineered wide host plasmid pRK290:pBR325: 14a:KmR:ADH, with the yeast alcohol dehydrogenase I gene (ADli) and the selectable kanamycin resistance marker from Tn5($Km^R$) at the subcloned T-DNA target site, was constructed in steps requiring the sequential construction of the intermediate plasmids pBR322:ADH:ColEl:Tn5 and pBR325:14a:$Km^R$: ADH. pBR322:ADH is a 3.4 Kb genomic clone of the yeast ADH I locus in the Bam HI site of pBR322 (Williamson et al., 1979; and Bennetzen and Hall, 1982, supra). ColEl:Tn5 is the plasmid ColEl containing the active transposon Tn5, and pBR325:14a is Bam HI fragment 14a of pTiT37 cloned in pBR325 (Matzke and Chilton, 1981, supra). The left and right sides of fragment 14a, surrounding the target site (Hpa I) are designated 14aL and 14aR, respectively. The enzymes used are denoted as follows: Bam HI, B; Eco RI, E; Hpa I, H; DNA polymerase I (large fragment), Pol I.

More specifically, the neomycin phosphotransferase gene from Tn5, which encodes kanamycin resistance ($Km^R$), was attached to the yeast gene in order to allow selection for the passenger DNA during the construction. For this purpose, ColEl::Tn5 was opened at a unique Bam HI site in the transposon but outside the $Km^R$ coding region and cloned into pBR322: ADH, a recombinant plasmid containing the 3.4 Kb ADH I gene in pBR322 (Bennetzen and Hall, 1982, supra). pBR322:ADH was opened at one of two Bam HI sites by partial endonuclease digestion. After analysis of digests of the resulting recombinant plasmids, there was chosen pBR322:ADH:ColEl::Tn5 which had the $Km^R$ coding region attached directly to the yeast genomic DNA (see FIG. 1). Digestion of pBR322:ADH:ColEl::Tn5 with the endonuclease Eco RI, treatment with Klenow polymerase to blunt the Eco RI cohesive ends, and Hpa I digestion to remove undesired vector DNA and both termini of Tn5 produced a blunt-ended DNA fragment containing the ADH I gene and a selectable antibiotic resistance marker (see FIG. 1). The fragment of Tn5 remaining in this construct is incapable of transposition (Jorgensen et al., Mol. Gen. Genet., 177:65–72, 1979).

The blunt-ended passenger DNA fragment encoding ADH I and $Km^R$ was inserted into the same target site in T-DNA of pTiT37 chosen by Matzke et al. (1981, supra), the Hpa I site in Bam HI 14a, available as a pBR325 recombinant plasmid. The construction scheme allowed direct selection for the desired product (pBR325:14a:$Km^R$:ADH, FIG. 1), which confers $Km^R$ from the target DNA and chloramphenicol resistance ($Cm^R$) from the pBR325 vector. To allow introduction of the resulting "engineered" DNA fragment into Agrobacterium tumefaciens, pBR325:14a:$Km^R$:ADH was recloned through unique Eco RI sites into the wide-host plasmid pRK290, (Ditta et al., Proc. Natl. Acad. Sci. 77:7347–51, 1980), to form pRK290:pBR325:14a:$Km^R$:ADH. This plasmid has the wide-host range and P1 incompatibility characteristics of pRK290.

pRK290:pBR325:14a:$Km^R$:ADH was introduced into Agrobacterium strain A208 by transformation (Holsters et al., Mol. Gen. Genet. 163:181–87, 1978). The resident Ti plasmid, pTiT37, contains the wild type counterpart of the engineered Bam HI 14a fragment in pRK290;pBR325:14a:$Km^R$:ADH. Homologous recombination can produce cointegrates between the two plasmids; a second recombination can produce an exchange reaction (see FIG. 2), resulting in the transfer of the $Km^R$: ADH insert onto the Ti plasmid, the desired event. To select for such recombinants plasmid incompatibility selection was used (Ruvkin and Ausubel, Nature, 289:85–88, 1980; Matzke and Chilton, 1981, supra), evicting pRK290 replicons with R751. pMG2, a P1 plasmid encoding gentamycin resistance ($Gm^R$) that can be introduced into A. tumefaciens by conjugation (Matzke & Chilton, 1981, supra). Selection for Agrobacteria with resistance to both gentamycin and kanamycin selects for homogenotization. Four independent colonies were chosen and cloned by three successive single colony isolations on selective plates.

Referring to FIG. 2, recombination ( . . . ) occurs naturally in Agrobacterium strain A208 between homologous regions of the engineered wide host plasmid pRK290:pBR325:14aKm$^R$:ADH and the resident Ti plasmid pTiT37. The result of a double crossing-over is a transfer of the ADH and $Km^R$ genes onto the Ti plasmid, with the unengineered target site being transferred to the wide host plasmid. Selection for the double crossing-over is provided by eviction of pRK290 replicons from A208 using an incompatible third plasmid, and selection for the retention of $Km^R$ (Matzke and Chilton, 1981, supra).

Ti plasmid DNA (pTiT37.ADH 1–4) was isolated from each of the four cloned strains produced above and analyzed by Southern hybridization to determine the structure of the T-DNA. The predicted T-DNA structure in all four strains (see FIG. 3) was confirmed by probing Bam HI digests of the Ti plasmid DNA with pBR325:14a:$Km^R$:ADH. Only the engineered Bam HI 14a fragments and the ADH I gene were detected. There was no visible hybridization to unaltered Bam HI 14a restriction fragments, nor was there hybridization to any DNA fragments of sizes representative of the free pRK290 or pBR325 vector fragments (see FIG. 3). It was concluded that the yeast DNA sequence and attached $Km^R$ were incorporated into the Ti plasmid by double recombination (see FIG. 4). All four clones of recombinant Agrobacteria were used in the parallel plant transformation experiments described hereinafter.

Figure 3:
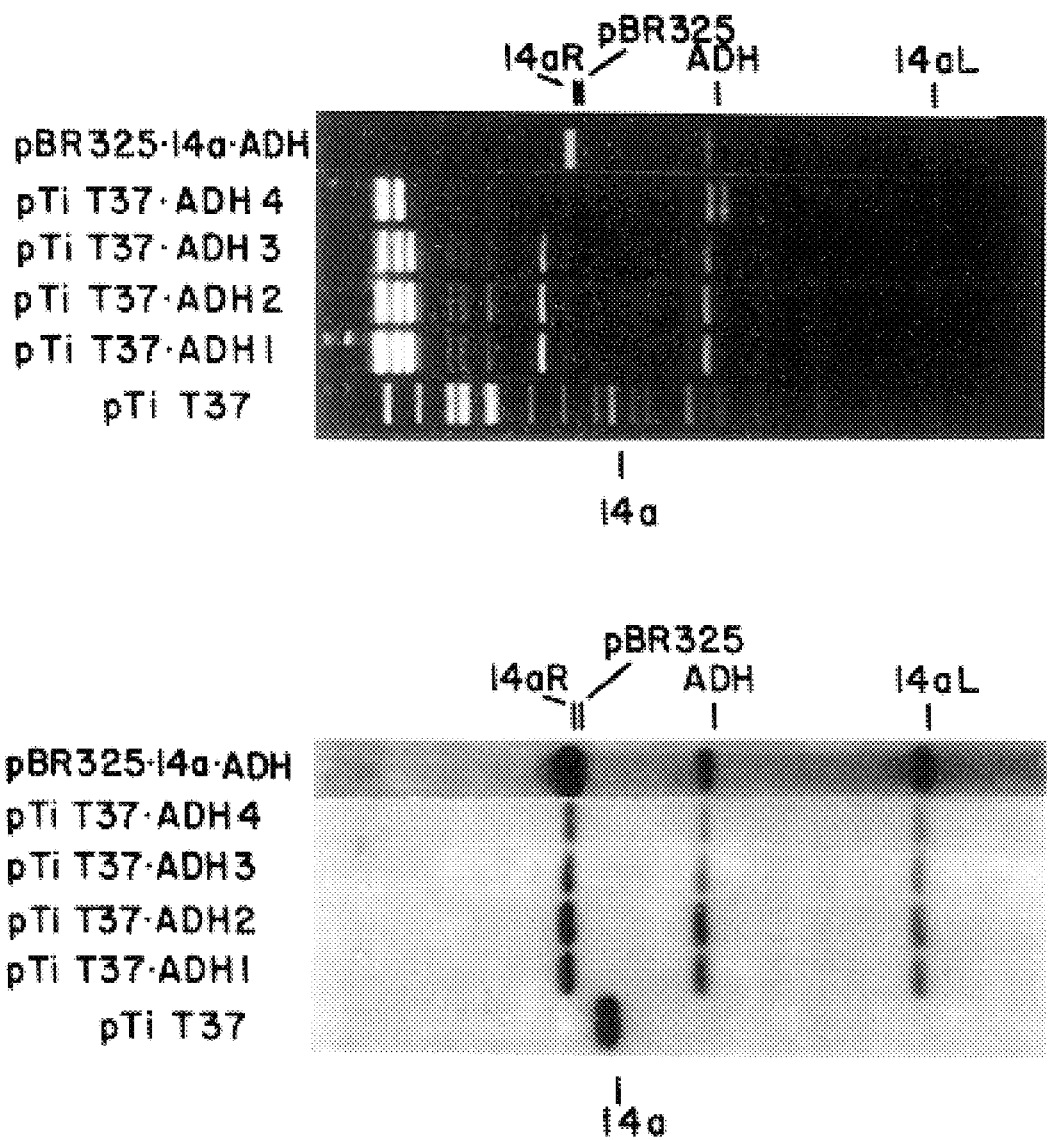
FIG. 3 shows the results of an analysis by Southern hybridization to determine the structure of T-DNA in Ti plasmid DNA (pTiT37.ADH 1–4) isolated from each of four cloned strains.

FIG. 3 shows the supporting confirmation of the structure of pTiT37.ADH plasmids. Plasmid DNA was digested with endonuclease Bam HI and electrophoresed on 0.6% agarose gels, with mobility of DNA from left to right as shown. Top of FIG. 3:gel stained with ethidium bromide. Bottom of FIG. 3:autoradiogram of the same gel following Southern analysis using nick-translated DNA of pBR325:14aKm$^R$:ADH as a hybridization probe. The structure of pBR325:14a:ADH is detailed in FIG. 1 as pBR325:14a:Km$^R$:ADH. pTi T37 is the resident Ti plasmid of Agrobacterium strain A208, and pTiT37.ADH1–4 are Ti plasmids from the four cloned Agrobacterium strains following engineering of pTiT37 as shown in FIGS. 1 and 2. Densely staining bands in pTiT37.ADH1–4 of the upper gel represent restriction fragments of the evicting plasmid R751.pMG 2, present in multiple copies in Agrobacterium (Matzke and Chilton, 1981, supra). Southern analysis shows that the unmodified fragment 14a in pTiT37 has been replaced with the engineered fragment in pTiT37.ADH1–4.

Figure 4:
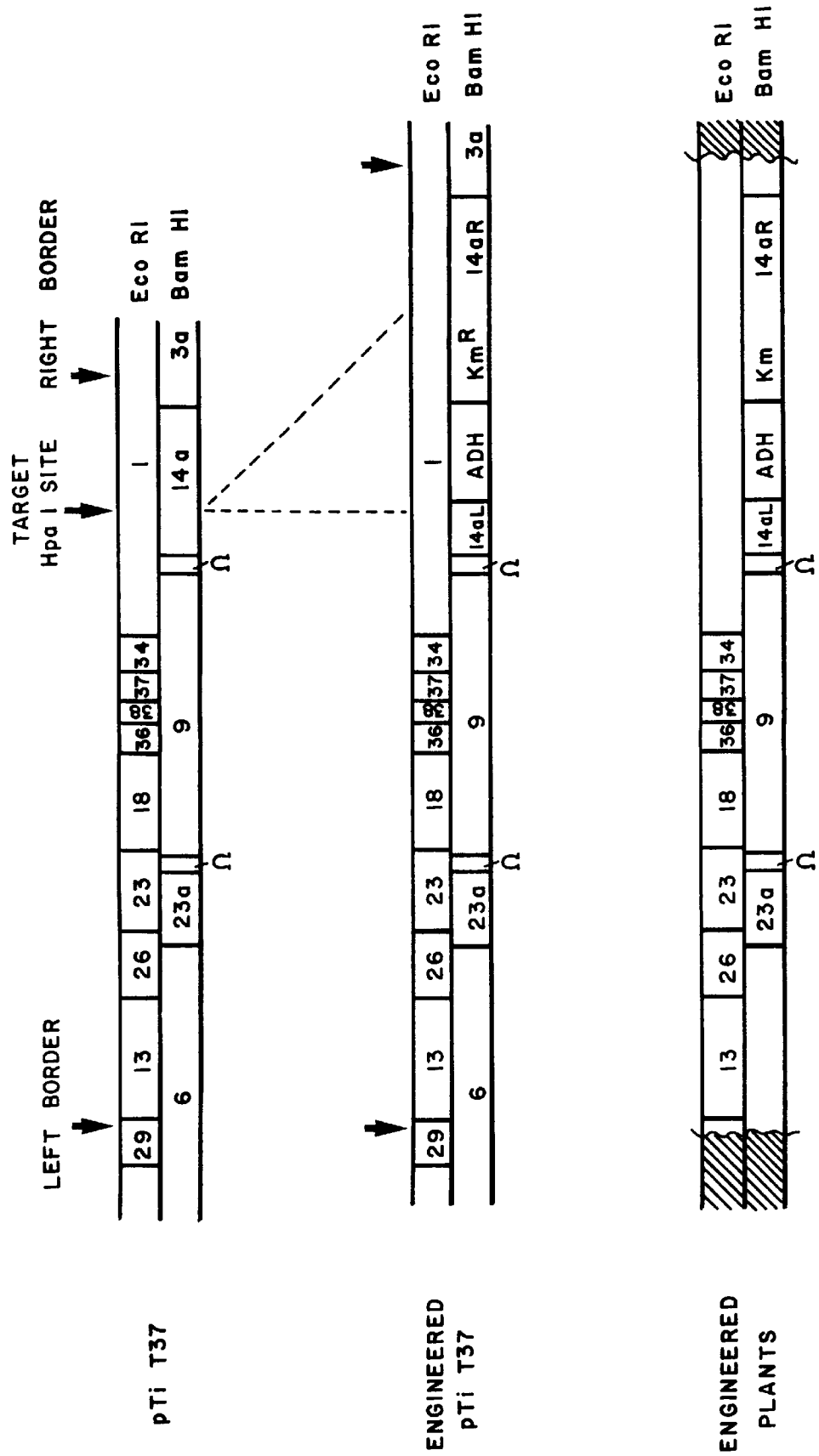
FIG. 4 shows restriction fragment maps of original and engineered T-DNA.

The restriction fragments of original and engineered T-DNA are shown in FIG. 4. At the top of FIG. 4, DNA restriction fragments found within the T-DNA of pTiT37 (region between left and right borders, approximately 22 Kb in length) following digestion with endonuclease Bam HI and Eco RI are shown. The target site for insertion of the new DNA is a unique Ilpa I restriction site within Bam HI fragment 14a (middle of FIG. 4). The restriction map of T-DNA on the engineered Ti plasmids is unchanged, with the exception of a 6.0 Kb insert into the target site. Insertion of the ADH and $Km^R$ genes into the target site provides two new Bam HI sites, resulting in the appearance of fragments 14aL, ADH, $Km^R$ and 14aR and the loss of Bam HI fragment 14a (bottom of FIG. 4). The restriction map of the T-DNA in transformed plants is identical to that present on the Ti plasmid, with the exception of the border-containing fragments. T-DNA borders within Eco RI fragment 29 and Bam HI fragment 3a join with plant DNA, resulting in loss of the original restriction fragments in those regions and creation of novel T-DNA/plant DNA junction fragments (Chilton et al., 1977).

Induction and Phenotype of Tumors from the Recombinant Ti Plasmids

For plant transformation and regeneration studies, there was employed isogenic A. tumefaciens strains carrying pTiT37.ADH 1–4, described above, and pTiT37.14a/a, a plasmid of similar structure containing the Hpa I subfragment of Tn5 as the passenger gene at the same T-DNA site (Matzke & Chilton, 1981, supra). All five engineered A. tumefaciens strains incited tumors on Kalanchoe daigremontiana stems but not leaves, incited roots on carrot discs, and did not incite tumors on intact or decapitated tobacco plants. The positive control strain, A208, carrying wild type pTiT37, produced tumors in all cases. To obtain transformed tobacco cells, an in vitro inoculation protocol was used.

The inoculation protocol involved the use of a technique developed by Braun, Cancer Res. 16:53–56 (1956) for transformation of stem segments in vitro. Stems of N. tabacum var. Havana 425 were surface sterilized with 7% commercial Clorox and 80% ethanol, rinsed with sterile distilled water and cut into 1 cm. long segments. These were placed basal end up in petri dishes containing Murashige and Skoog medium (Murashige and Skoog, Physiol. Plant. 15:473–497, 1962)(MS medium) without hormonal supplement. The basal end was then inoculated with bacteria, puncturing the cut surface of the stem by syringe needle. After 5–8 days of incubation at 25° with 16 hr. light, callus developed at the upper surface of all stem segments including those inoculated with avirulent strain A136. The callus regions were then transferred to hormone-free MS medium containing carbenicillin (200 ug/ml). After 3 transfers at 4 week intervals on this medium, the tissues were free of bacteria and could be assayed for growth and nopaline content.

Tobacco cells inoculated with the engineered Agrobacteria produced nopaline and characteristically grew very slowly on hormone free medium unless roots formed, in which case growth was considerably stimulated. Regardless of whether the cultures formed roots or not, they were extremely friable when cultured on hormone free medium, an attribute that facilitated single cell cloning. Tissues of tumor lines HADH2 (H425 tobacco transformed by the pTiT37.ADH2 bacterial strain), HADH4 and H14A/a, when shaken briefly in liquid culture medium, proved a good source of single cells. These cells were plated and grown under non-selective conditions (i.e.in medium supplemented with auxin and cytokinin) and clones were screened for nopaline. Considerable variation in the frequency of transformed clones obtained was observed. From HADH2, 39 of 48 clones were nopaline positive, whereas only 2 of 40 from HADH4 and 2 of 45 from H14a/a respectively, were nopaline positive.

As to the biological characteristics of the cloned plant cell lines, briefly, the nopaline positive clones exhibited the characteristics of the non-cloned lines. Growth on homone free medium was extremely slow (see FIG. 5) and was accelerated by root formation, though fewer roots initiated spontaneously in the cloned lines than in the parental lines. For rapid growth of the cloned lines, it was necessary to supplement the medium with a cytokinin such as kinetin; auxin, in contrast, was not required. At high levels of kinetin (0.3 mg/l or higher) clones from HADH2 and H14a/a regularly formed buds (see FIG. 6), thereby mimicking the phenotype of tobacco cells transformed by the wild-type T37 strain. An important difference, however, was that buds from the HADH2 and H14a/a transformed clones were capable of regenerating roots and growing into complete plants (see FIGS. 5 and 6). Buds from cells transformed by wild type T37 T-DNA never form roots and must be grafted onto healthy host plants in order to reach maturity (Braun and Wood, Proc. Natl. Acad. Sci. 73:496–500, 1976). Complete plants were derived from HADH2, HADH4, and H14a/a clones, although the HADH4 clones yielded highly abnormal buds that root very poorly. All plants and buds tested contain nopaline, evidence of T-DNA presence in the regenerated tissue.

Figure 5:
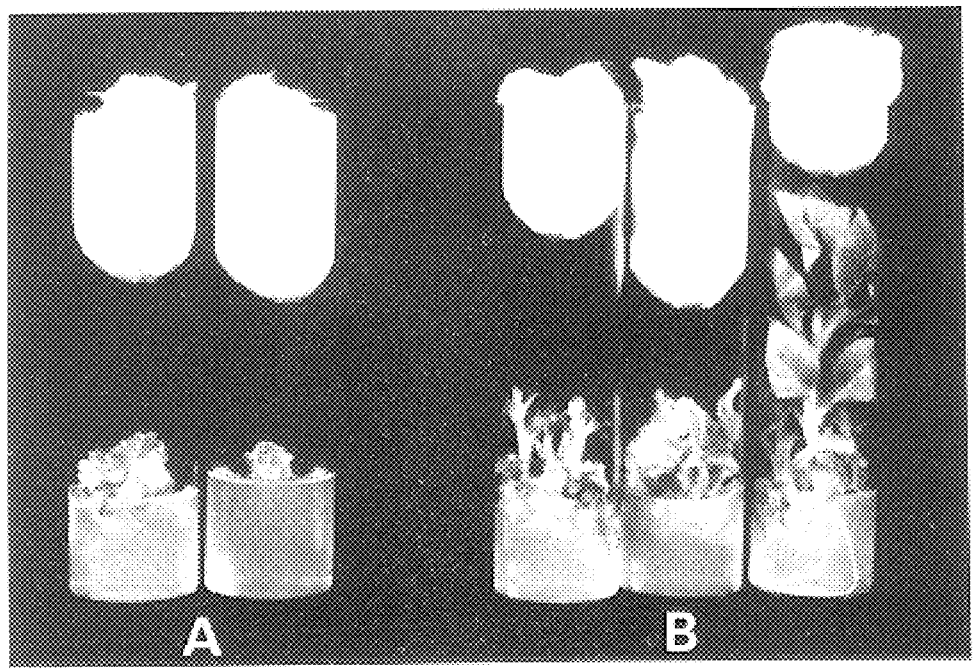
FIG. 5 is a photograph showing the growth of transformed tobacco tissue on medium with and without cytokinin.

The growth of transformed tobacco tissue on medium with and without cytokinin is shown in FIG. 5. Tobacco cells transformed with wild-type pTiT37 or engineered pTiT37.ADH Ti plasmids display varied hormonal requirements. Above A in FIG. 5 is shown tissue grown for four weeks on basal MS medium (Murashige and Skoog, 1962, supra) of pTiT37 transformed H425 tobacco cells (left) or pTiT37.ADH2 transformed cells, clone #5 (right). Above B in FIG. 5 is shown tissue grown for five weeks on basal MS medium supplemented with 0.3 mg/l kinetin: at the left, clone #41 of pTiT37.14/a transformed cells; in the center, clone #5 of pTiT37.ADH2 transformed tobacco cells; at the right, clone #24 of pTiT37.ADH2 transformed cells.

Figure 6:
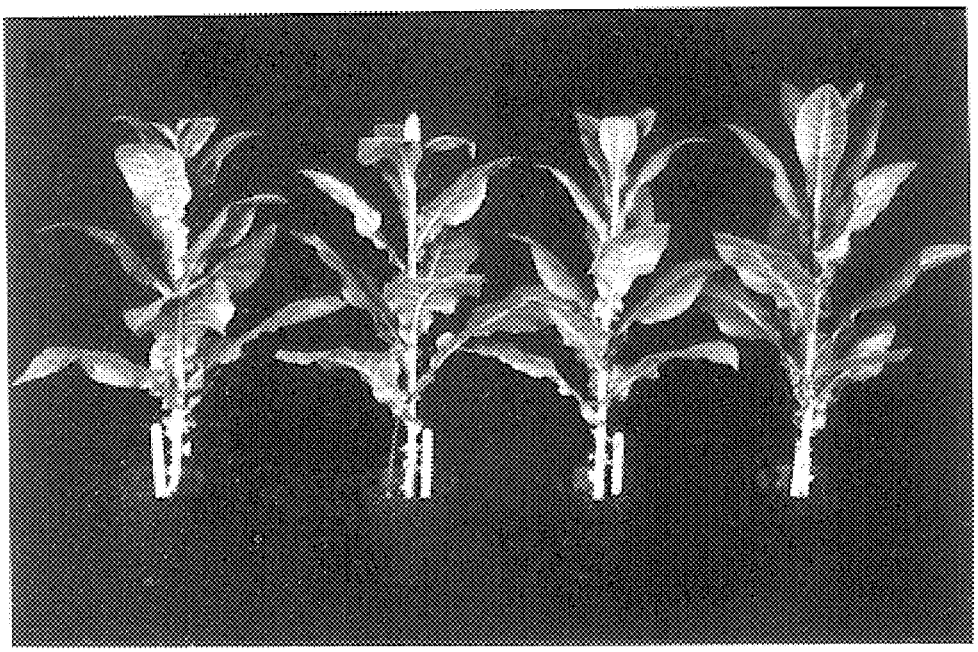
FIG. 6 is a photograph showing regenerated plants and progeny from transformed tobacco cells.

In FIG. 6, the regenerated plants and progeny from transformed tobacco cells are shown. From left to right, Havana 425 tobacco grown from seed, 11 weeks old; plant #25 regenerated from HADH2 clone #24 cells, 10 weeks; nopaline positive progeny grown from seed of self pollinated HADH2 clone #24 plant #2, 12 weeks; nopaline negative progeny grown from seed of HADH2 clone #24 plant #2, 12 weeks.

DNA From Regenerated Plants Contains the ADH I Gene

All plants with roots regenerated from crown gall tumors by earlier investigators have been found to exhibit large deletions covering most or all of T-DNA. (Yang and Simpson, Proc. Natl. Acad. Sci., 78:4151–55, 1981 and Leemans et al., EMBO Journal 1:147–152, 1982). In the regenerated plants of this invention, the synthesis of nopaline in all tissues indicated that the right border region of T-DNA, which contains the gene encoding nopaline synthase, was still present in the plants. In the case of the HADH2 plants, the ADH I DNA and selective marker had been inserted into T-DNA approximately 3 Kb to the left of the 3' end of the nopaline synthase transcript (Bevan and Chilton, J. Mol. Appl. Genet., 1982).

Figure 7:
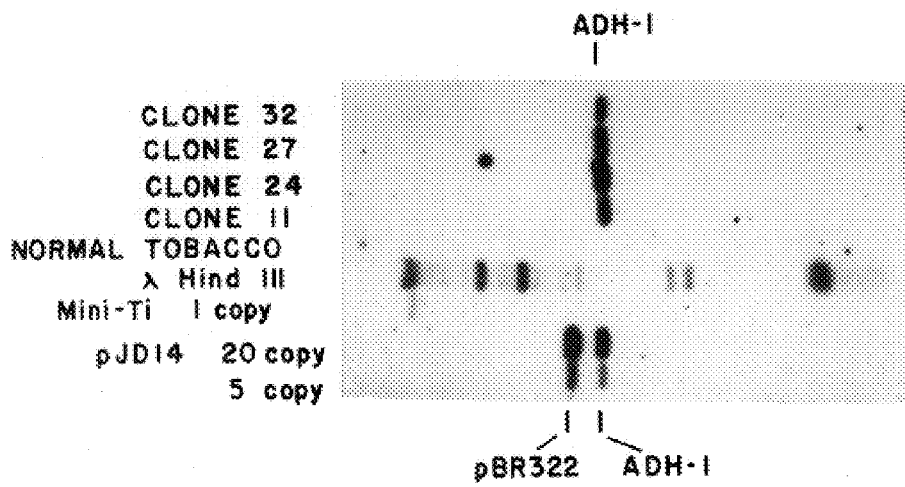
FIG. 7 depicts the results of an analysis by Southern hybridization showing that regenerated plants contain the yeast ADH I gene.

FIG. 7 shows that regenerated plants produced in accordance with the invention contain the yeast ADH I gene. DNA was isolated from normal Havana 425 tobacco, and from plants regenerated from cloned cultures #11, 24, 27 and 32 of tobacco transformed with engineered pTiT37.ADH2. The DNA was digested with endonuclease Bam HI, electrophoresed on 0.6% agarose gels, and transferred to nitrocellulose for Southern analysis. The hybridization probe used was nick-translated pBR322: ADH, a clone of yeast ADH I in pBR322 (Bennetzen and Hall, 1982, supra). Mini-Ti, a clone of T-DNA with partial homology to pBR322, was electrophoresed at a concentration corresponding to 1 copy per genome equivalent. pJD14(pBR322: ADH, Bennetzen and Hall, 1982, supra) is present at 5 copies and 20 copies per genome equivalent. Mobility of DNA on gels was left to right as shown. As shown in FIG. 7, the yeast DNA and flanking Bam HI sites are present in all four plants examined. In fact, the DNA appears to be present in all clones at approximately 20 copies per genome equivalent. The probe does not hybridize to normal tobacco DNA (see FIG. 7).

The Entire T-DNA is Present in the Regenerated Plants

To determine whether any deletion of T-DNA had occurred, DNA from the regenerated plants was digested with endonucleases Bam HI and Eco RI for Southern analyses and probed with a plasmid (Mini-Ti) containing the entire T-DNA plus some flanking DNA of pTiT37. The probe lacks any homology with the yeast ADH insert, which therefore does not produce a band in FIG. 8. A comparison of FIG. 8 (a and b) with the T-DNA fragment map (FIG. 4) confirms that all internal T-DNA restriction fragments are found in the DNA of plants from the four clones examined. In the analysis of Eco RI digested plant DNAs (FIG. 8a), fragments 13, 18, 23, 26, 34, and 36–38 are visible while the 1.5 Kb Eco RI fragment 29 and the 21 Kb engineered Eco RI fragment 1 (1'), are not seen. This indicates that T-DNA borders are in Eco RI fragments 29 and 1' as expected. The plant DNA exhibits two novel Eco RI restriction fragments of approximately 15 Kb and 25 Kb, that represent right border fragments (Lemmans et al., J. Mol. Biol. 144:353–376, 1980) as determined below. The Bam HI digest of plant DNA exhibits bands of hybridization at the position of all expected internal T-DNA fragments. In addition, novel fragments are present at 2.1 Kb, 10 Kb, and 12 Kb; the 2.1 Kb fragment is a right border and the 10 Kb fragment is a left border, as described below. One hybridizing restriction fragment (approximately 7.5 Kb) appears in both normal and transformed plant DNA.

Examination of the T-DNA Borders

The DNA of the transformed plants was further analyzed by Southern hybridizations using T-DNA border clones as probes, in order to determine whether the new restriction fragments represent junctions between plasmid and plant DNA. A 3.0 Kb Ti plasmid subclone (Hind III fragment 23) containing the right border, 2 Kb of T-DNA, and 1 Kb of flanking Ti plasmid DNA hybridizes to both the 15 Kb and 25 Kb novel Eco RI restriction fragments, although neither fragment is identical in size to the engineered Eco RI fragment 1 of the original transforming plasmid.

Figure 8A:
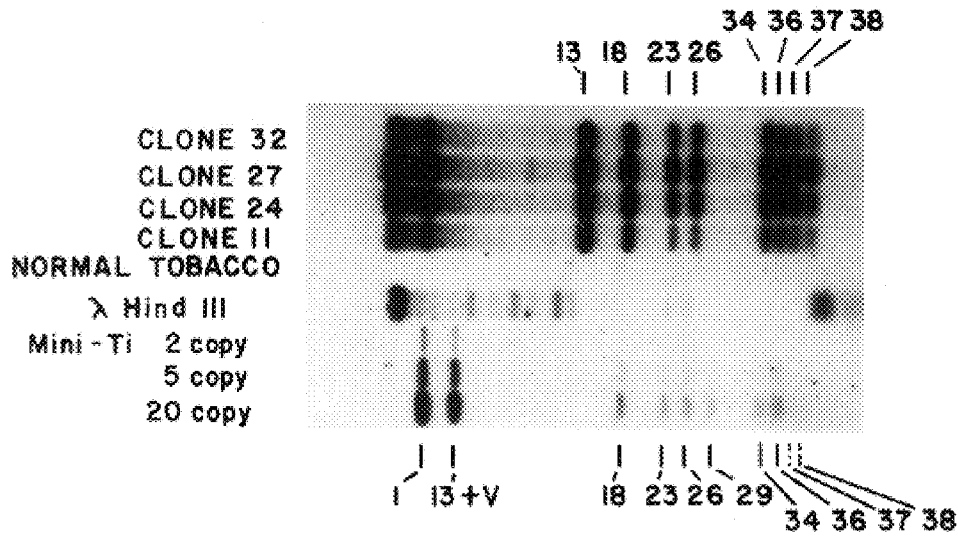
FIGS. 8a and 8b depict the results of an analysis by Southern hybridization showing that regenerated plants contain full length T-DNA.
Figure 8B:
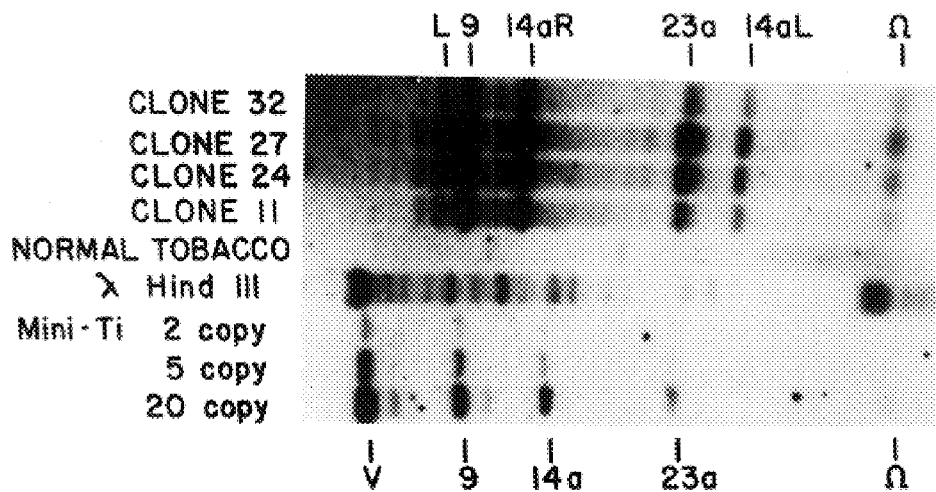

The left border of pTiT37 T-DNA is located near the right end of Eco RI fragment 29 (see FIG. 4) which is therefore not present as an internal fragment in the transformed plants (see FIG. 8a). The failure to observe bands assignable as left border fragments in Eco RI digests of the plant DNA is expected because of the relatively short region of T-DNA (57 bp) present on the junction fragment (Yadav et al., Proc. Natl. Acad. Sci. 79:6322–6326, 1982). Probing of a Bam HI digest with the Hind III fragment 23 (containing the right T-DNA border) showed hybridization to the right-hand portion of Bam HI fragment 14a, but also to the novel 2.1 Kb fragment seen in FIG. 8b, which was therefore interpreted as a T-DNA/plant DNA border fragment. These combined with those of the Eco Ri digest described above, are consistent with the idea that the predicted right end of T-DNA has integrated into plant DNA, and that at least 2 new plasmid DNA/plant DNA border fragments have resulted.

Probing of Bam HI digested DNA with a left border-containing Ti plasmid subclone (Bam HI fragment 6) revealed a single fragment of 10 Kb, slightly larger than the 9.5 Kb Bam HI fragment 6. No hybridization was seen to the 12 Kb Bam HI fragment, which has not yet been identified. Because only 40% of a junction fragment of this size should be homologous to the hybridization probe, the relative intensities of bands in FIG. 8b suggest that the border fragment is present in the plant genome in approximately as many copies as the internal T-DNA fragments.

R1 Seedlings Contain Nopaline

Plants derived from clones HADH2 and H14A/a were allowed to flower, were self-pollinated, and set seed. Nopaline assays of the germinated R1 seedlings from one plant of HADH2 cloned cells showed that 46 of 200 seedlings examined contain nopaline, with relative levels of nopaline varying greatly among the nopaline positive plants.

The T-DNA is Present in Germinated R1 Seedlings

Figure 9:
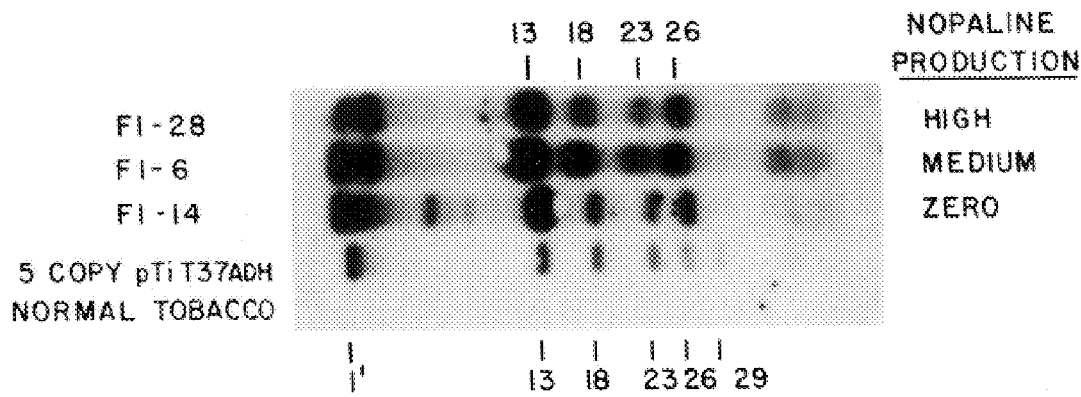
FIG. 9 depicts the results of Southern hybridization analysis showing that T-DNA is present in R1 progeny of engineered plants.

The presence of nopaline in some of the R1 progeny indicated that at least a portion of T-DNA had survived meiosis. To determine whether deletions had occurred in the T-DNA of the progeny, there was carried out Southern analysis of DNA isolated from young seedlings containing a high level, medium level or zero nopaline. Analysis of Eco RI digests (see FIG. 9) or Bam HI digests confirmed that all contain complete and multiple copies of the original transforming T-DNA, including the nopaline synthase gene. Copy number of the T-DNA appears to be similar in the three different seedlings, and does not appear to correlate with the level of nopaline production.

In the above-detailed experimental work, the $^{32}$P-dCTP (spec. act. 400 Ci/mmole), the restriction endonucleases, DNA polymerase (Klenow fragment), T4 DNA ligase and antibotics were obtained from commercial suppliers.

The following experimental procedures were used:

The genomic clone of yeast alcohol dehydrogenase I in pBR322 (pJD14) was provided by J. Bennetzen (Bennetzen and Hall, 1982a, b, supra). *Agrobacterium tumefaciens* strain A208 is a transconjugant containing Ti plasmid pTiT37 in the cured strain C58 genetic background (Sciaky et al., Plasmid, 1:238–53, 1978). The plasmid ColEl::Tn5 was obtained from D. Berg. pBR325(Bam HI 14a) is a recombinant plasmid containing the T-DNA fragment Bam HI fragment 14a of pTiT37 (Yadav et al., 1980, supra). Wide host range plasmid pRK290, provided by D. Helinski, is in the P1 incompatibility group, and is a nonconjugative but mobilizable derivative of RK2 (Ditta et al., 1980, supra). R751.pMG2, a recombinant derivative of R751 and pMG2 and also of the P1 incompatibility group, was supplied by G. Jacoby. The plasmid pTiT37.14a/a, constructed by Matzke and Chilton (1981), supra, is an insertional mutant of pTiT37.

Bacterial Growth Media

L-broth (1% tryptone, 1% NaCl, 0.5% yeast extract) and YEP broth (1% peptone, 1% yeast extract, 0.5% NaCl) were used for liquid cultures of *E. coli* and *A. tumefaciens*, respectively. *E. coli* strains were plated on L-broth containing 1.5% agar and appropriate antibiotics. *A. tumefaciens* strains were plated on Nutrient Agar (Difco) supplemented with appropriate antibiotics.

Plasmid DNA Isolation

*E. coli* plasmids were isolated and purified on CsCl/ ethidium bromide density gradients as reported previously (Matzke and Chilton, 1981, supra). Ti plasmid was prepared by the method of Currier and Nester (J. Bacteriol., 126:157–65 1976), except that shearing of the lysate was not carried out (Matzke and Chilton, 1981, supra).

Conjugations and Transformation of Bacterial Cells

Transformations of *E. coli* and Agrobacterium were carried out as previously described (Matzke and Chilton, 1981, supra). Conjugation between *E. coli* and *A. tumefaciens* was accomplished by combining 0.2 ml L-broth and 0.2 ml each of rapidly growing *E. coli* (strain HB101 containing gentamycin resistant R751-pMG2) and *A. tumefaciens* (containing pTiT37 and the kanamycin resistant engineered wide host plasmid). After 2–4 hr incubation without agitation at 30° C., cells were plated on nutrient agar supplemented with kanamycin (100 µg/ml) and gentamycin (50 µg/ml), and incubated at 30° C. Individual colonies appeared in approximately 48 hours, and were picked and cloned by three successive single colony isolations on plates containing kanamycin and gentamycin.

Inoculation of Tobacco Stems by Recombinant Bacteria

*A. tumefaciens* strains with insertional mutations at the Hpa I restriction site of fragment Bam HI 14a did not induce tumors on tobacco when inoculated by needle puncture into intact plants. For isolation of transformed tobacco cells, we used the technique developed by Braun (1956) for transformation of stem segments in vitro. Stems of *N. tabacum* var. Havana 425 were surface sterilized with 7% commercial Clorox and 80% ethanol, rinsed with sterile distilled water and cut into 1 cm long segments. These were placed basal end up in petri dishes containing Murashige and Skoog medium (Murashige and Skoog, 1962, supra) (MS medium) without hormonal supplement. The basal end was then inoculated with bacteria, puncturing the cut surface of the stem by syringe needle. After 5–8 days of incubation at 25° C. with 16 hr light, callus developed at the upper surface of all stem segments including those inoculated with avirulent strain A136. The callus regions were then transferred to hormone-free MS medium containing carbenicillin (200

μg/ml). After 3 transfers at 4 week intervals on this medium, the tissues were free of bacteria and could be assayed for growth and nopaline content.

Plant Tissue Culture and Cloning

Once free of inciting bacteria, plant tissues were grown on MS medium at 25° C. with 16 hr light and 8 hr dark. These tissues were cloned using a suspension method described previously (Binns and Meins, Planta, 145:365–369, 1979). Briefly, tissues were placed in liquid MS medium supplemented with 0.02 mg/l naphthalene acetic acid (NAA) and shaken at 135 rpm and 25° C. for 2–3 days. The resultant suspensions were filtered successively through 543 and 213 μm stainless steel mesh, concentrated and plated at a final density of $8 \times 10^3$ cells/ml in 5 ml of MS medium containing 0.5% agar, 2.0 mg/l NAA, 0.3 mg/l kinetin and 400 mg/l yeast extract (Difco). Good suspensions of individual cells were obtained from the tumors transformed by recombinant bacterial strains and routinely gave 30–50% plating efficiency. Once colonies had reached 1 mm in diameter they were picked by scalpel point and placed on complete MS medium (i.e. supplemented with 2.0 mg/l NAA and 0.3 mg/l kinetin). After these had grown to approximately 50 mg, colonies were split into 3 pieces. One was placed on hormone free MS medium, one on complete MS medium, and the third piece was placed on MS supplemented with 5 mM arginine to be used for nopaline analysis (Otten and Schilperoort, Biochem. Biophys. Acta 527:497–500, 1978).

Regeneration of Recombinant Plants

Tissues from various nopaline positive clones were transferred onto MS medium supplemented with 0.3 mg/l kinetin, and cultured at 25° C. with 16 hr light and 8 hr dark. Shoots initiated were subsequently rooted by placing them in a medium consisting of 1/10 strength MS salts, no sucrose or hormones, 0.4 mg/l thiamine and 1.0% agar, with the pH adjusted to 7.0. Rooted plantlets were transferred to soil and placed at high humidity in a greenhouse. After 7–10 days, the plants were then grown with normal greenhouse conditions.

Plant DNA Isolation

High molecular weight DNA was isolated as described (Chilton, et al., Nature, 295:432–34, 1982) from young tobacco plants frozen in liquid nitrogen and ground in a mortar with pestle. Following banding in CsCl-ethidium bromide gradients, dye was extracted with isopropyl alcohol equilibrated with 20X SSC (3M NaCl, 0.3M sodium citrate), an equal volume of 0.6M sodium acetate was added, and DNA was precipitated by the addition of absolute ethanol to a final concentration of 70%.

Southern Hybridization Analysis of DNA

Plant or plasmid DNA was digested to completion with restriction endonucleases and loaded into 1×8×8 mm wells in a horizontal 0.65% agarose gel prepared in Tris-acetate buffer (Chilton et al., supra, 1977). Electrophoresis, transfer of DNA to nitrocellulose, and Southern hybridizations were carried out as described by Thomashow, et al., Proc. Natl. Acad. Sci., 77:6448–52 (1980). For analyses of Ti plasmid structure in Agrobacterium, a total of 2 μg plasmid DNA was loaded per gel track, with standard plasmid digests run on the same gel at 0.1 μg per track. For plant genomic analyses, plant DNA was loaded at 10 μg per gel track; standard plasmid digests corresponded to the indicated genome equivalents (Chilton et al., supra, 1977). All standard plasmid digests on plant genomic DNA gels were digested with endonucleases and electrophoresed in the presence of 10 μg calf thymus DNA per track as carrier. Hybridization probes were generated by nick-translation of purified plasmid DNA, to a specific activity of approximately $10^8$ cpm/μg DNA.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A method of transforming a dicotyledonous plant susceptible to transformation by Agrobacterium, comprising:

contacting the plant with an *Agrobacterium tumefaciens* bacterium comprising a gene vector, the vector comprising DNA foreign to the Agrobacterium, and the vector not comprising a functional cytokinin autonomy gene.

2. A method for producing a morphologically and developmentally normal dicotyledonous plant comprising non-Agrobacterium foreign DNA stably integrated in the plant's genome, said method comprising the following steps:

a) transforming a dicotyledonous plant cell susceptible to transformation by Agrobacterium with an Agrobacterium-derived gene vector, said vector comprising non-Agrobacterium foreign DNA and the vector not comprising a functional cytokinin autonomy gene; and b) regenerating said transformed plant cell to produce a morphologically and developmentally normal transformed plant with said foreign DNA stably integrated in the plant's genome.

3. The method of claim 2, further comprising deriving a plant comprising said foreign DNA stably integrated in its genome from said plant regenerated from said plant cell transformed with said foreign DNA.

4. The method of claim 2, further comprising producing viable seed or seeds comprising said foreign DNA from said transformed plant.

5. A method for producing a transgenic dicotyledonous plant comprising a stably integrated non-Agrobacterium foreign DNA, the method comprising:

sexually propagating a dicotyledonous plant comprising non-Agrobacterium foreign DNA stably integrated into its genome, said foreign DNA having been introduced into the genome by an Agrobacterium-derived gene vector not comprising a functional cytokinin-autonomy gene; and selecting for progeny plants which comprise the non-Agrobacterium foreign DNA stably integrated into the genome of said progeny plants.

6. A method for producing a transgenic dicotyledonous plant comprising stably integrated non-Agrobacterium foreign DNA, the method comprising:

sexually propagating a dicotyledonous plant comprising non-Agrobacterium foreign DNA stably integrated into its genome, said plant derived from a dicotyledonous plant which was transformed by Agrobacterium-mediated transformation with a gene vector comprising said non-Agrobacterium foreign DNA and not comprising a functional cytokinin autonomy gene; and obtaining a progeny plant which comprises the non-Agrobacterium foreign DNA stably integrated into its genome.

7. A method for producing a transgenic dicotyledonous plant comprising stably integrated non-Agrobacterium foreign DNA, the method comprising:

propagating a dicotyledonous plant comprising non-Agrobacterium foreign DNA stably integrated into its genome, said plant derived from a dicotyledonous plant which was transformed by Agrobacterium-mediated transformation with a gene vector comprising said non-Agrobacterium foreign DNA and not comprising a functional cytokinin autonomy gene; and obtaining a plant which comprises the non-Agrobacterium foreign DNA stably integrated into its genome.

8. A method for producing a transgenic dicotyledonous plant comprising stably integrated non-Agrobacterium foreign DNA, the method comprising:

growing a seed of a dicotyledonous plant comprising non-Agrobacterium foreign DNA stably integrated into its genome, said plant derived from a dicotyledonous plant which was transformed by Agrobacterium-mediated transformation with a gene vector comprising said non-Agrobacterium foreign DNA and not comprising a functional cytokinin autonomy gene.

9. A method for producing seed of a transgenic dicotyledonous plant comprising stably integrated non-Agrobacterium foreign DNA, the method comprising:

propagating a dicotyledonous plant comprising non-Agrobacterium foreign DNA stably integrated into its genome, said plant derived from a dicotyledonous plant which was transformed by Agrobacterium-mediated transformation with a gene vector comprising said non-Agrobacterium foreign DNA and not comprising a functional cytokinin autonomy gene; and harvesting seed from said propagated plant.

10. A method of transforming a dicotyledonous plant of a species that is a naturally susceptible host for Agrobacterium, comprising:

contacting the plant with an Agrobacterium bacterium comprising a gene vector, the vector comprising DNA foreign to the Agrobacterium and the vector not comprising a functional cytokinin autonomy gene.

11. A method for producing a transgenic dicotyledonous plant comprising non-Agrobacterium foreing DNA stably integrated in the plant's genome, said method comprising the following steps:

a) transforming a cell of a dicotyledonous plant species that is a naturally susceptible host for Agrobacterium by Agrobacterium-mediated transformation with a gene vector comprising non-Agrobacterium foreign DNA and not comprising a functional cytokinin autonomy gene; and b) regenerating said transformed plant cell to produce a normal transformed dicotyledonous plant with said foreign DNA stably integrated in the plant's genome.

12. The method of claim 11, further comprising deriving a dicotyledonous plant comprising said foreign DNA stably integrated in its genome from the normal transformed dicotyledonous plant.

13. The method of claim 11, further comprising producing viable seed or seeds comprising said foreign DNA from the normal transformed dicotyledonous plant.

14. A method for producing a transgenic dicotyledonous plant comprising a stably integrated non-Agrobacterium foreign DNA, the method comprising:

sexually propagating a dicotyledonous plant comprising non-Agrobacterium foreign DNA stably integrated into its genome, said plant derived from a dicotyledonous plant which is of a species that is a naturally susceptible host for Agrobacterium and which was transformed by Agrobacterium-mediated transformation with a gene vector comprising said non-Agrobacterium foreign DNA and not comprising a functional cytokinin autonomy gene; and obtaining a progeny plant which comprises the non-Agrobacterium foreign DNA stably integrated into its genome.

15. A method for producing a transgenic dicotyledonous plant comprising a stably integrated non-Agrobacterium foreign DNA, the method comprising:

propagating a dicotyledonous plant comprising non-Agrobacterium foreign DNA stably integrated into its genome, said plant derived from a dicotyledonous plant which is of a species that is a naturally susceptible host for Agrobacterium and which was transformed by Agrobacterium-mediated transformation with a gene vector comprising said non-Agrobacterium foreign DNA and not comprising a functional cytokinin autonomy gene; and obtaining a plant which comprises the non-Agrobacterium foreign DNA stably integrated into its genome.

16. A method for producing a transgenic dicotyledonous plant comprising stably integrated non-Agrobacterium foreign DNA, the method comprising:

growing a seed of a dicotyledonous plant comprising non-Agrobacterium foreign DNA stably integrated into its genome, said plant derived from a dicotyledonous plant which is of a species that is a naturally susceptible host for Agrobacterium and which was transformed by Agrobacterium-mediated transformation with a gene vector comprising said non-Agrobacterium foreign DNA and not comprising a functional cytokinin autonomy gene.

17. A method for producing seed of a transgenic dicotyledonous plant comprising stably integrated non-Agrobacterium foreign DNA, the method comprising:

propagating a dicotyledonous plant comprising non-Agrobacterium foreign DNA stably integrated into its genome, said plant derived from a dicotyledonous plant which is of a species that is a naturally susceptible host for Agrobacterium and which was transformed by Agrobacterium-mediated transformation with a gene vector comprising said non-Agrobacterium foreign DNA and not comprising a functional cytokinin autonomy gene; and harvesting seed from said propagated plant.

18. An Agrobacterium-mediated method for genetically engineering a dicotyledonous plant comprising:

a) producing a transgenic plant cell by transforming a cell of dicotyledonous plant species that is a naturally susceptible host for Agrobacterium with a gene vector comprising non-Agrobacterium foreign DNA and not comprising a functional cytokinin autonomy gene by *Agrobacterium tumefaciens*-mediated transformation; and b) regenerating a whole normal plant from the transgenic plant cell which contains said foreign DNA stably integrated into its genome.

19. The method of claim 18, which further comprises propagating the whole normal plant to obtain seed.

20. A method for producing a transgenic dicotyledonous plant comprising intact T-DNA comprising non-Agrobacterium foreign DNA stably integrated into the genome of said plant, the method comprising:

propagating a dicotyledonous plant comprising non-Agrobacterium foreign DNA stably integrated into its genome, said plant derived from a dicotyledonous plant which is of a species that is a naturally susceptible host for Agrobacterium and which was transformed by Agrobacterium-mediated transformation with a disarmed T-DNA gene vector comprising said non-Agrobacterium foreign DNA and not comprising a functional cytokinin autonomy gene; and obtaining a plant which comprises the intact T-DNA stably integrated into its genome.

* * * * *

UNITED STATES PATENT AND TRADEMARK OFFICE
CERTIFICATE OF CORRECTION

PATENT NO. : 6,051,757
DATED : April 18, 2000
INVENTOR(S) : Barton et al.

It is certified that error appears in the above-identified patent and that said Letters Patent is hereby corrected as shown below:

On the title page,

Following the first paragraph concerning the cross-reference to related applications, the following paragraph should be inserted:

--The U.S. Government has rights in this invention, including a paid-up license to this invention and the right in limited circumstances to require the patent owner to license others on reasonable terms, as provided for by the terms of Contract No. DE-AC02-81ER10889 awarded by the U.S. Department of Energy.--

In Column 6, line 45, "(ADli)" should read --(ADH)--.

In Column 7, line 50, "(...)" should read --(---)--.

In Column 11, line 67, "antibotics" should read --antibiotics--.

In Column 15, line 43, "foreing" should read --foreign--.

Signed and Sealed this

Twenty-seventh Day of February, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO.   : 6,051,757                                          Page 1 of 1
DATED        : April 18, 2000
INVENTOR(S)  : Barton et al.

It is certified that error appears in the above-identified patent and that said Letters Patent is hereby corrected as shown below:

<u>Title page,</u>
Item [73], should read:
[73] Assignee: -- and Competitive Technologies, Inc. --

<u>Column 1,</u>
Line 3, should read:
-- The present invention was made under Grant PCM81-04064 from the National Science Foundation. The Government may have certain rights to the invention. --

Signed and Sealed this

Fourth Day of February, 2003

JAMES E. ROGAN
*Director of the United States Patent and Trademark Office*